United States Patent [19]

Luria

[11] 4,169,677
[45] Oct. 2, 1979

[54] METHOD AND APPARATUS FOR DIAGNOSING THE CONDITION OF OIL-WETTED PARTS

[75] Inventor: David Luria, Tel Aviv, Israel
[73] Assignee: Panel Laboratories Ltd., Ramat Aviv, Israel
[21] Appl. No.: 793,755
[22] Filed: May 4, 1977

[30] Foreign Application Priority Data

May 3, 1976 [IL] Israel .................................... 49518

[51] Int. Cl.² ...................... G01N 33/28; G01N 15/04
[52] U.S. Cl. ........................................... 356/70; 73/64; 73/432 PS
[58] Field of Search .................... 356/70, 102; 233/46; 73/64, 432 PS, 424, 61.4, 425.4 R, 61 R

[56] References Cited

U.S. PATENT DOCUMENTS

| | | | |
|---|---|---|---|
| 1,232,104 | 7/1917 | Sharples | 233/46 |
| 2,450,603 | 10/1948 | Lomasney | 73/64 |
| 2,817,970 | 12/1957 | Whitby | 73/432 PS |
| 2,956,434 | 10/1960 | Donoghue | 73/432 PS |
| 3,091,124 | 5/1963 | Hindman | 73/425.4 P |
| 3,955,423 | 5/1976 | Ohringer | 73/425.4 R |
| 3,981,584 | 9/1976 | Guymer | 356/70 |

FOREIGN PATENT DOCUMENTS 145060 4/1962 U.S.S.R. ................................. 73/61 R

OTHER PUBLICATIONS

ASTM "1965 Book of ASTM Standards" Part 17, ASTM Designation: D893–607, Tentative Method of Test for Insolubles in Used Lubricating Oils, pp. 362–366.
Spinco, "An Introduction to Density Gradient Centrifugation" Spinco Tech Reviews, 1960, Beckman Inst. Co. Spinco Div., Palo Alto, Calif. pp. 1–27.

*Primary Examiner*—John K. Corbin
*Assistant Examiner*—Wm. H. Punter
*Attorney, Agent, or Firm*—Benjamin J. Barish

[57] ABSTRACT

A method and apparatus are described for diagnosing the condition of oil-wetted parts subject to wear, wherein a specimen of the used oil from the part is extracted, and a plurality of samples are separated according to the different mobility rates of its particles through a liquid medium during the centrifuging of the specimen through the liquid medium for a predetermined period of time. The samples are then analyzed to determine their compositions, thereby providing an indication of the identities of the wearing parts and their rates-of-wear. In one described embodiment, the specimen is centrifuged for a sufficiently long predetermined time to stratify the particles according to size and density; and in a second described embodiment, the specimen is centrifuged for a plurality of short predetermined time periods during each of which a sample of the particles passing the complete length of the liquid medium is removed and analyzed. In both embodiments, the samples are separated by passing them through a large mesh screen at the bottom end of the holder in which the centrifuging is effected.

10 Claims, 4 Drawing Figures

METHOD AND APPARATUS FOR DIAGNOSING THE CONDITION OF OIL-WETTED PARTS

BACKGROUND OF THE INVENTION

The present invention relates to a method and apparatus for diagnosing the condition of oil-wetted parts subject to wear, such as internal combustion engines, bearings, valves, and the like.

Techniques are known for analyzing used oils to diagnose the condition of oil-wetted parts subject to wear, particularly internal combustion engines. The commonly used technique is to extract a specimen of the oil from the oil-wetted part and to analyse it, for example by spectrometric analysis, to determine the composition of the particles in the oil specimen; this provides an indication of the parts from which the particles were derived and therefore the parts subject to the wear. A serious drawback of the known technique, however, is that the procedure merely identifies the total quantity of each of the chemical elements in the specimen contributed by an alloy which is contained in the specimen. Therefore it is difficult to identify the part suffering the major wear, or to determine its rate of wear, particularly when the part includes a number of alloys of similar constituents. Thus if the system being diagnosed includes two or more alloys with similar constituents, with one part being of large size and exhibiting a normal rate of wear, and another part being of small size and exhibiting an abnormally high rate of wear, it is difficult or impossible to determine whether the system as a whole is exhibiting an abnormally high rate of wear in any of its parts, because of the "shielding" influence one element of one part exhibits on the same element of another part.

Another drawback in the conventional technique is that in order to make a life prediction of the part, at least two tests at different time periods of use are required, because the life of the part depends on the "rate" of wear.

SUMMARY OF THE INVENTION

An object of the present invention is to provide a method and apparatus for diagnosing the condition of oil-wetted parts having improvements in the above respects.

According to a broad aspect of the invention, there is provided a method of diagnosing the condition of oil-wetted parts subject to wear, comprising the steps of: extracting a specimen of the used oil from the oil-wetted parts; separating the specimen with a plurality of samples according to the different mobility rates, due to the differences in size and density of the particles through a liquid medium during the centrifuging of the specimen through the liquid medium for a predetermined period of time; and analysing said samples to determine the composition of the particles in each, thereby providing an indication of the identities of the wearing parts and their rates-of-wear.

The centrifuging is effected in a holder containing the liquid medium. The specimen is introduced into one end of the holder, and the plurality of samples are separated by passing them through a screen at the opposite end of the holder, which screen is of larger mesh than the largest particles in the specimen and provides a uniform dispensing of each sample for analysis.

In the preferred embodiment of the invention described below, the liquid medium is clean oil.

The speed of movement of particle in a liquid medium such as oil may be presented, according to "Stoke's Law," as follows:

$$V = K(\rho_1 - \rho_2)gd^2/\eta$$

wherein
$\eta$ = viscocity of the oil
$\rho_1$ = density of the alloy
$\rho_2$ = density of the oil
$g$ = gravity
$d$ = diameter of particle.
$K$ = constant It will thus be seen that the mobility of the particles in the oil is related to their densities and to the square of their diameters. The density of a particle is related to its composition; and the diameter or size of a particle is directly related to its rate-of-wear, since parts having low rates of wear produce small size particles and parts having high rates of wear produce large size particles. Thus, the procedure of the invention enables a discrimination to be made according to the composition of the parts from which they are derived, and also according to the size of the particles, indicative of the rate-of-wear of the parts from which they are derived. This discrimination permits a better identification to be made of the wearing part producing the particles present in the oil specimen; and also a better determination of the rate-of-wear or wear condition, of such parts even by a single test, and therefore a better prediction as to the probable remaining life of such parts.

The foregoing technique is to be distinguished from the previously known technique, such as disclosed in U.S. Pat. No. 3,981,584, wherein the sample of oil taken from the equipment is passed through various filters to separate wear particles of various sizes, to thereby determine the particle size distribution in the samples in order to ascertain the state of wear of the equipment. In such a known technique, the discrimination is made only in accordance with particle size, whereas in the present technique it is made also in accordance with density, since density also affects the mobility rate. This additional discrimination permits a better identification to be made of the wearing part and the rate-of-wear or wear condition of such particles even by a single test.

Two embodiments of the invention are described below. In one, the specimen is centrifuged for a sufficiently long period of time sufficient to stratify the particles within the liquid medium according to size and density, the stratifications in the oil medium being then separated into the plurality of samples.

In a second described embodiment, the specimen is centrifuged for a plurality of short predetermined periods of time, and a sample which includes particles passing the whole length of the liquid medium is removed after each short period of centrifuging.

According to another aspect of the invention, there is provided apparatus for diagnosing the condition of oil-wetted parts in accordance with the above method, comprising: a holder having an open upper end and an open lower end; the holder being fillable with the liquid medium followed by the application of the oil specimen on top of the liquid medium; a removable plug closing the upper end of the holder; a removable cap closing the lower end of the holder; and a screen of larger mesh than the largest particles disposed across the open lower end of the holder between same and said cap.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
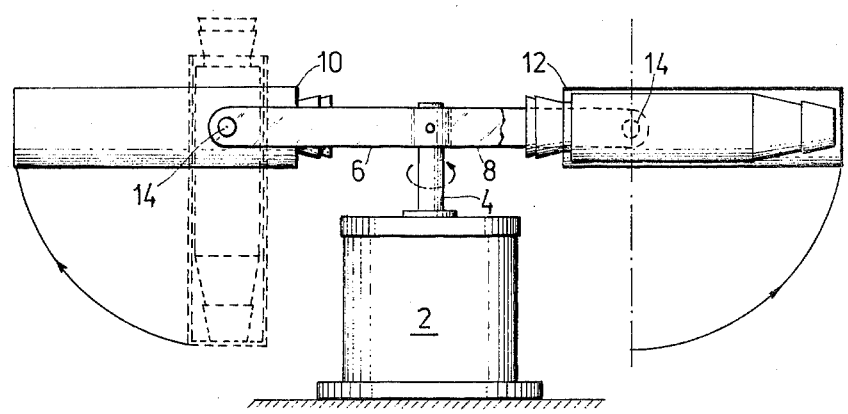
FIG. 1 diagrammatically illustrates centrifuging apparatus which may be used in practising the method of the present invention.

The centrifuging apparatus illustrated in FIG. 1 is generally of conventional construction, including a drive motor 2 rotating a vertical shaft 4, which shaft in turn rotates a pair of horizontal arms 6 and 8 carrying a specimen holder 10, 12 at each end. Each specimen holder is pivotally mounted to its respective arm, as shown by pivotal mounting 14 with respect to holder 12 on its arm 8, so that when the centrifuge is not operating, the specimen holder normally assumes the vertical (broken-line) position, and when the centrifuge is operating, the holder is pivoted by the centrifugal force to assume the horizontal (full-line) position.

Figure 2:
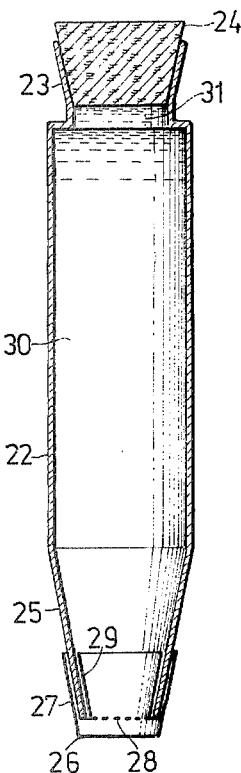
FIG. 2 illustrates one form of specimen holder that may be used in the centrifuging apparatus in one stage of the method.
Figure 3:
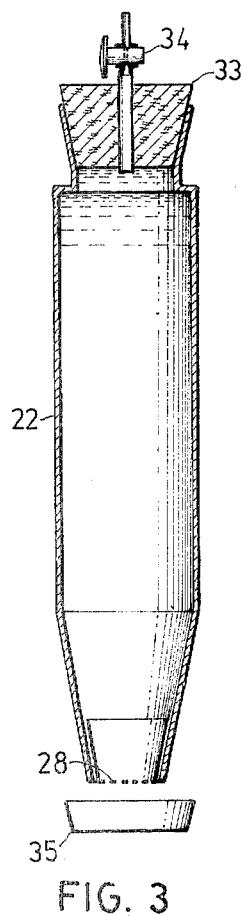
FIG. 3 illustrates the specimen holder of FIG. 2 in a second stage of the method.

In one embodiment of the invention, which may be implemented by the use of the specimen holder 22 in FIGS. 2 and 3, the specimen is centrifuged through a liquid medium, preferably oil, for a substantial period of time sufficient to stratify the particles within the liquid medium according to size and density; and then the stratifications in the liquid medium are separated into a plurality of samples. For this purpose, the specimen holder 22 is generally of tubular shape, open at both ends. Its upper end is formed with a conical neck 23 receiving a plug 24, and its lower end 25 is also conical and receives a removable closure cap 26 having conical side walls 27 receivable over the outer conical surface 25 of holder 22. The lower end further includes a screen 28 carried by a conical sleeve 29 receivable within the conical surface 25 of the holder. Screen 28 is thus disposed across the open lower end of the holder 22 above cap 26. The mesh of screen 28 is larger than the largest particles normally expected to be present in the oil specimen to be analysed.

In using the holder for performing the method according to the invention, screen 28 and cap 26 are applied across the lower end 25 of the holder 22, and the holder is then filled with clean oil 30 to the mouth of neck 23, as shown in FIG. 2. The oil specimen to be analysed is introduced on top of the clean oil, this oil specimen being indicated as 31 in FIG. 2, and plug 24 is then inserted into neck 23 so that the holder is completely filled with the clean oil 30 and the oil specimen 31 on top of it.

Holder 22 containing the clean oil 30 and the oil specimen 31 are then centrifuged by the apparatus illustrated in FIG. 1 for a substantial interval of time, for example for about 5 hours. This causes the particles within the specimen 31 to distribute themselves in the oil medium 30 according to their different mobility rates in the medium, which rates are directly related to the density of the particles and to the square of their diameters in accordance with "Stokes Law" as discussed above.

After the centrifuging operation has been completed, plug 24 is removed and replaced by plug 33 (FIG. 3) containing an on-off valve 34. In addition, cap 26 is removed from the lower end of the holder 22 and the holder is held above a dish or container 35 for receiving a sample of the centrifuged specimen. On-off valve 34 is turned on to permit a sample of the oil and specimen to drop by gravity into holder 35. The valve is then turned off and another container 35 is placed under the holder 22 to receive another sample by turning-on valve 34. In this manner, a plurality of samples, for example about 25, are deposited in serial fashion in a plurality of containers 35.

The samples are then tested, e.g. by spectrometric analysis, to determine their contents.

It is desired to include screen 28 to close the lower end of the holder 22 particularly when a relatively high viscocity oil is used for the liquid medium 30, as this tends to produce a more uniform flow of the oil and specimen particles to the container 35 when valve 34 is opened.

It will be appreciated that the sample deposited in the first container 35 will be the lowermost stratum of the centrifuged oil 30 and specimen 31; i.e., it will include the particles in the original oil specimen 31 which have travelled the greatest distance during the centrifuging operation; whereas the sample received in the last container will be the highermost stratum and will include the particles which travelled the least distance during the centrifuging operation. The first sample will thus contain the particles of larger size and higher density as described above in connection with "Stokes Law." Accordingly, a discrimination is made as to particle size and density. This discrimination is very helpful in determining not only the identification of the wearing parts from which the particles have been removed, but also the rate of wear of such parts, which is helpful in making a prediction of the life of the part.

Figure 4:
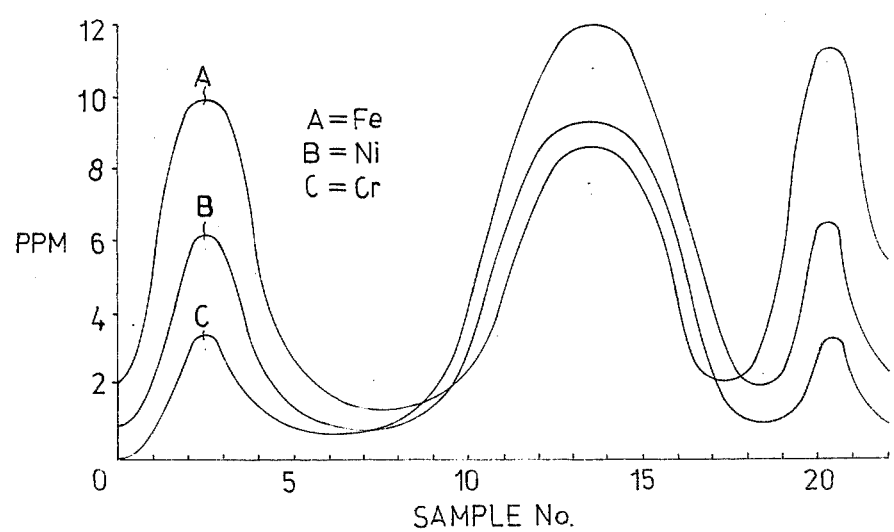
FIG. 4 is a curve diagram illustrating typical test results obtainable by practising the method of the invention.

FIG. 4 is a diagram illustrating typical test results that may be produced by the practice of the method. Each curve in FIG. 4 indicates another chemical element; for example, Curve A might indicate iron; Curve B might indicate nickel; and Curve C might indicate chromium. It will be seen that Sample 3 and 4, being the earlier samples and therefore containing the particles of highest mobility, have relatively high contents of iron, nickel and chromium, the content of iron being the highest and that of chromium being the lowest. Intermediate Samples 14 and 15 also have high metal contents, the proportion of chromium (Curve C) in these samples being the highest, and that of iron (Curve A) being the lowest. Finally, Sample 21 also has a high metal content, the content of iron (Curve A) being the highest and that of nickel (Curve B) being the lowest. It has been found that the "bunching effect" illustrated in FIG. 4, wherein the metal particles tend to "bunch" in distinct layers in the centrifuged, oil and specimen, is a common occurrence in practicing this method.

The foregoing data obtained by the above-described procedure is helpful in not only identifying the parts which produced the particles in the oil specimen being analysed, but also the rate-of-wear of such parts, and thereby better enables a prediction to be made as to the life of the parts or device (e.g. engine) whose condition is being diagnosed.

To improve the accuracy of the life of prediction of the parts being diagnosed, the above procedure could be first followed for producing reference data with respect to reference parts, and then followed with respect to working parts for producing test data with respect to the working parts. The preliminary reference data would be produced by following the procedure with respect to a number of different reference parts having different periods of useful life. The test data produced with respect to the working part whose condition is being diagnosed would be compared with the reference data to see with which reference data it best matches; since the useful lives of all the reference parts are known in the reference data, a better prediction can thus be made as to the ultimate life of the working part whose condition is being diagnosed.

To further improve the accuracy of the life prediction, a modified procedure may be used in testing the working part whose condition is being diagnosed. In this modified procedure, the specimen is centrifuged for a plurality of short periods of time rather than a single long period as in the above-described procedure, and a sample which includes particles passing through the whole length of the liquid medium in the holder is removed after each short period of centrifuging.

For example, the holder 22, containing the clean oil medium 30 and the oil specimen 31, may be centrifuged for about 5 minutes (rather than 5 hours as in the previously-described procedure) after which time cap 26 is removed, and a new cap 26 filled with new clean oil is applied. The sample contained in the removed cap 26 would include, within the oil liquid medium, the particles from the specimen 31 which travelled through the whole length of the liquid medium during the five-minutes of centrifuging. These particles would be those having the higest mobility according to "Stokes Law" in which particle size and particle density are factors as discussed above. The holder would then be centrifuged with the new cap 26 for another short period of time, e.g. 5 minutes, and the cap including its contents would be removed and used as a second sample to be tested. The procedure would be repeated as many times as desired to produce any desired number of samples. For example, the procedure could be repeated to produce about 100 samples, which would provide very detailed data from which there could be made a reasonably accurate diagnosis as to the condition of the part being diagnosed, and also a reasonably accurate prediction as to the useful life of the part.

In this modified testing procedure, screen 28 holds-back the oil medium and particles from flowing through the bottom end of the holder 22 during the time between the removal of the cap 26 and its sample after one centrifuging period, and the application of a new cap filled with new clean oil for receiving a new sample during the next centrifuging period.

Many other variations, modifications and applications of the described embodiments of the invention may be made.

What is claimed is:

1. A method of diagnosing the condition of oil-wetted parts subject to wear, comprising the steps of: extracting a specimen of the used oil from the oil-wetted parts; introducing said specimen into one end of a holder containing a liquid medium; separating the particles in the specimen into a plurality of samples according to the different mobility rates, due to difference in size and density, of the particles through the liquid medium during the centrifuging of the specimen and liquid medium in the holder for a predetermined period of time; said plurality of samples being separated by passing the particles and liquid medium through a screen at the opposite end of the holder, which screen is of larger mesh than the largest particles in the specimen to provide a uniform dispensing of the samples through said opposite end of the holder; and analysing said samples to determine the composition of the particles in each, thereby providing an indication of the identities of the wearing parts and their rates-of-wear.

2. The method according to claim 1, wherein said liquid medium is clean oil.

3. The method of claim 1, wherein said specimen is centrifuged for a predetermined period of time sufficiently long to stratify the particles within the liquid medium according to size and density, the stratifications in the liquid medium being then separated into the plurality of samples.

4. The method according to claim 3, wherein the stratifications in the liquid medium are separated after centrifuging by dispensing the stratified liquid medium and particles contained therein through said opposite end of the holder serially into a plurality of separate sample containers.

5. The method according to claim 4, wherein the stratified liquid medium and particles after centrifuging are dispensed through the lower end of the holder by controlling an on-off valve at the upper end of the holder.

6. The method according to claim 1, wherein said specimen is centrifuged for a plurality of successive short predetermined periods of time, and a sample which includes particles passing the whole length of the liquid medium is removed after each such short period of centrifuging.

7. The method according to claim 6, wherein a sample is separated during each centrifuging operation into a sample container attached to said opposite end of the holder before the centrifuging operation and removed therefrom after the centrifuging operation.

8. The method according to claim 7, wherein after each centrifuging operation the sample container attached to the lower end of the holder is filled with new clean liquid medium.

9. Apparatus for diagnosing the condition of oil-wetted parts by separating particles in a specimen thereof into a plurality of samples according to the different mobility rates, due to differences in size and density, of the particles through a liquid medium during the centrifuging of the specimen, comprising: a holder having an open upper end and an open lower end; the holder being fillable with the liquid medium followed by the application of the oil specimen on top of the liquid medium; a removable plug closing the upper end of the holder; a removable cap closing the lower end of the holder; and a screen of larger mesh than the largest particles disposed across the open lower end of the holder between same and said cap.

10. Apparatus according to claim 9, further including a second removable plug containing an on-off valve, which second removable plug is to be substituted for the first-mentioned one after the centrifuging operation for dispensing the oil medium and particles through the lower end of the holder to produce said plurality of samples.

* * * * *